US006709678B2

(12) United States Patent
Gruber

(10) Patent No.: US 6,709,678 B2
(45) Date of Patent: *Mar. 23, 2004

(54) EASY TO SWALLOW ORAL MEDICAMENT COMPOSITION

(75) Inventor: Peter Gruber, Freiburg (DE)

(73) Assignee: Losan Pharma GmbH, Neuenburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,167

(22) PCT Filed: Aug. 14, 1997

(86) PCT No.: PCT/CH97/00299

§ 371 (c)(1),
(2), (4) Date: Feb. 10, 1999

(87) PCT Pub. No.: WO98/06385

PCT Pub. Date: Feb. 19, 1998

(65) Prior Publication Data

US 2002/0068088 A1 Jun. 6, 2002

(30) Foreign Application Priority Data

Aug. 15, 1996 (CH) ................................................ 2006/96

(51) Int. Cl.$^7$ .............................. A61K 9/28; A61K 9/36
(52) U.S. Cl. ...................... 424/490; 424/494; 424/493; 424/474; 424/475; 424/476; 424/479; 424/480; 424/481; 424/492; 424/495; 424/496; 424/497; 424/482; 427/2.14; 427/2.15; 514/200; 514/198; 514/165
(58) Field of Search .................................. 424/490, 492, 424/493, 494, 495, 496, 497, 466, 464, 474, 475, 479, 480, 481, 482, 476; 427/2.14, 2.15

(56) References Cited

U.S. PATENT DOCUMENTS

| 4,882,169 | A | | 11/1989 | Ventouras | 424/493 |
| 5,051,262 | A | | 9/1991 | Panoz et al. | |
| 5,288,500 | A | | 2/1994 | Ibsen | 424/489 |
| 5,366,738 | A | * | 11/1994 | Rork et al. | 424/473 |
| 5,460,825 | A | * | 10/1995 | Roche et al. | 424/470 |
| 5,464,633 | A | | 11/1995 | Conte et al. | |

FOREIGN PATENT DOCUMENTS

| EP | 0281513 | 9/1988 |
| EP | 0662320 | 7/1995 |
| GB | 9403617 | 6/1996 |
| WO | 8806893 | 9/1988 |
| WO | 9301800 | 2/1993 |

* cited by examiner

Primary Examiner—Russell Travers
Assistant Examiner—Shahnam Sharareh
(74) Attorney, Agent, or Firm—Leydig, Voit & Mayer, Ltd.

(57) ABSTRACT

An oral composition which is adapted to be dispersed in an aqueous carrier substantially immediately prior to administration comprises a multiplicity of particles comprising an active substance, the particles being combined with one or more gelling or swelling agents capable of forming a viscous medium around the particles in an aqueous carrier as well as being provided with a masking surface layer when dispersed in the aqueous carrier. This serves to mask uneven surfaces on the particles and prevent them from adhering to oral mucosa when the composition is ingested and thus makes it easier to administer large dosages of an active substance. The masking surface layer is preferably provided by an increased viscosity of the viscous medium in the immediate vicinity of the particles relative to the viscosity of the surrounding aqueous carrier. A ready-to-use composition is prepared by mixing the composition with an aqueous carrier substantially immediately prior to administration of the composition.

12 Claims, No Drawings

EASY TO SWALLOW ORAL MEDICAMENT COMPOSITION

This is a 371 of PCT/CH97/00299 filed on Aug. 14, 1997 which claims priority to Swiss Application 2006/96.

The invention relates to an easy to swallow pharmaceutical composition for oral administration comprising at least one pharmaceutically active compound in an effective amount and comprising one or more coated particles, and to a process for the production thereof and a method for treating or preventing diseases.

Oral intake of solid medicament compositions, such as tablets or capsules, is associated with problems in particular as a function of their size, it frequently being possible for swallowing difficulties to occur, especially in children and elderly people. Although simultaneous administration of several tablets or capsules may improve swallowability, on the other hand it has an adverse effect on patient compliance. Alternative formulations have already been proposed to get around these problems, for example powders or granules, which are made into suspensions, tablets which disintegrate in the mouth, or chewable tablets. Tablets which disintegrate in the mouth and chewable tablets are, however, generally not very suitable for active ingredients with an unpleasant taste or for medicinal products with delayed release of active ingredient, because the coatings present for this purpose are unavoidably damaged by the tabletting process or the chewing action. On the other hand, in the case of suspensions, the particles rapidly settle out and can usually be taken only incompletely on drinking, which leads to unacceptable variations in the dose. This problem cannot be eliminated in a satisfactory manner by increasing the viscosity, because an appropriately viscous liquid is drunk only reluctantly.

EP-A 0 313 328 describes effervescent tablets or water-dispersible tables with delayed release of active ingredient, which are obtained by compressing release-slowed particles with an effervescent material or other water-dispersible ingredients and in which the release-slowed particles have a coating containing a water-swellable acrylic polymer and a water-soluble hydroxylated cellulose derivative. Both types of tablets disintegrate in water or in the mouth, and the released particles can be swallowed together with the ancillary substances. However, as a consequence of the disintegration of the tablet, individual particles may remain in the glass or in the mouth, whereby deviations from the required dose may occur, or there is the risk that active ingredients with an unpleasant taste may be released in the mouth. In addition, the release characteristics may be adversely affected, depending on the content of water-soluble hydroxylated cellulose derivative, and the active ingredient may be released too quickly.

In a similar way, EP-A 0 459 695 proposes that active ingredient particles be coated, to mask the taste and/or delay release, with a mixture comprising cellulose acetate and/or cellulose acetate butyrate and hydroxypropylcellulose, although the coated particles are preferably compressed to a chewable tablet. However, these have the disadvantage—as do the aforementioned effervescent tablets and water-dispersible tablets—that the release-slowing coatings or taste-masking masking coatings are partly damaged by the tabletting process, whereby the release characteristics are altered in an unwanted manner, or active ingredients with an unpleasant taste may be released in the mouth, which may lead to the patient refusing the product.

By contrast, WO-A 93/01800 recommends coating microgranules of a bioactive substance (in particular a protein) and a weak base only partly with a material which delays release in the mouth and in the stomach, and mixing the partly coated microgranules with a particle size of from 50 to 500 μm with an acidifier which yields a pH of from 1.5 to 6 in solution, and with a gel-forming agent. The only partial enteric coating is intended to ensure, together with the pH buffering, that inactivation of the bioactive substance is avoided and, on the other hand, gradual release in the small intestine is ensured.

Pellets or granule particles with a taste-masking coating are also reported in WO-A 91/16043. The coated particles can be packed into sachets together with a polymer (xanthan gum), sweeteners and flavourings. In a similar way, BR-A 9 403 617 further recommends that medicinal products with an unpleasant taste be produced in the form of micropellets with a natural or synthetic coating, and these be mixed with thickeners, sweeteners, flavourings and colours.

By contrast, EP-A 0 662 320 describes a mixture of up to 40% by weight of a medicinal product which can be administered orally, at least 3% by weight of a gelling agent such as pregelatinized starch and up to 5% by weight of a binder as dry gel composition, which is intended on mixing with twice to fifteen times the amount of water to yield a homogeneous gruel-like gel. In the case of bitter active ingredients, it is recommended additionally to use a masking agent such as propylene glycol, glycerol or polyethylene glycol or a taste improver such as potassium glutamate or sodium inosinate or—alternatively—to powder the active ingredient and coat with a masking agent.

U.S. Pat. No. 4,882,169 proposes coated pellets with a diameter of from 0.2 to 3.0 mm which form a completely homogeneous dispersion in water and which have a core containing microparticles of at least one pharmaceutically active substance, where appropriate one or more release-controlling or taste-masking coatings and a swellable outer layer. The latter contains a swellable polymer, preferably guar gum. Since the swellable materials rapidly swell and disintegrate in water, they must be sprayed with an adhesive solution so that they adhere to the pellets. The coated pellets are packed together with guar gum granules and flavourings into sachets from which they can be removed and dispersed in water.

U.S. Pat. No. 5,288,500 likewise proposes combining a multiplicity of active ingredient-containing particles, which can preferably be coated with a diffusion-controlling layer and have a diameter of from 0.05 to 7 mm, with a gelling or swelling agent. The latter can be mixed with the active ingredient-containing particles, be present in a coating, be added to the active ingredient-containing particles before mixing with an aqueous vehicle, or be dispersed in an aqueous vehicle to which the active ingredient-containing particles are added. The proposed formulation is dispersed in an aqueous vehicle and is intended to form a smooth surface around each dispersed particle, whereby irregularities on the surface of the particles are to be masked and adhesion of the particles to the vessel or to the oral mucosa is to be prevented.

Suitable gelling or swelling agents for the formulations proposed in U.S. Pat. No. 5,228,500 are substances, especially hydrophilic polymers, which form colloidal dispersions, sols or suspensions in an aqueous medium. They are employed in an amount which is sufficient to mask the irregularities on the surfaces of the dispersed particles, but is not so large that the dispersibility in an aqueous vehicle might be adversely affected. If required, the viscosity in the immediate vicinity of the dispersed particles can be influenced by salt formation, chelate formation, changing the polarity and the like. However, the intention is to avoid an almost solid gel being formed by the complete formulation. The components of the formulation can be kept separate until administered or be packed together in sachets or processed to tablets or capsules; for oral administration, they are dispersed together in an aqueous vehicle.

The formulations described in WO-A 91/16043, BR-A 9 403 617, EP-A 0 662 320, U.S. Pat. Nos. 4,882,169 and 5,288,500 are taken together with an aqueous vehicle in which they are dispersed before the administration. The formulations disintegrate into the individual particles therein, which means that quantitative intake is no longer ensured as a rule. This is true even if the dispersed particles—as in the case of the formulations disclosed in U.S. Pat. No. 5,288,500—have a smooth surface and are intended not to adhere to the vessel or the oral mucosa. This is because, in general, the drinking of a particle suspension or dispersion represents a real problem because, as a rule, at least some of the particles remain on the bottom of the vessel after the solution has been completely drunk, and can be transferred only with difficulty into the mouth, and because it is in every case very uncertain whether the patient will in fact attempt this.

In addition, particle suspensions or dispersions cannot, as a rule, be swallowed quantitatively. Even if the particles have a smooth surface which does not adhere to the oral mucosa, it is not in general possible to prevent the dose being swallowed only incompletely and, for example, individual particles may remain stuck between the teeth. This problem is—apart from the unwanted deviations from the intended dose—a crucial disadvantage, especially with active ingredients with an unpleasant taste, because many active ingredients such as, for example, ciprofloxacin, loperamide, cimetidine, ranitidine, acemetacin, diclofenac sodium, ibuprofen, naproxen and indomethacin are so extremely bitter that quantitative transfer of the taste-masked particles into the stomach is absolutely necessary. For example, a single ciprofloxacin particle dissolving in the mouth would on its own produce such a bitter, unpleasant taste that the product will be rejected by the patient. However, since on the other hand the swellable polymer has only limited suitability for masking the taste, because of the required dispersibility in water, the previously disclosed products for active ingredients with an unpleasant taste are unsuitable or at best suitable only if the particles have additional taste-masking coatings.

The formulations disclosed in WO-A 91/16043, BR-A 9 403 617, EP-A 0 662 320, U.S. Pat. Nos. 4,882,169 and 5,288,500 are thus associated with the disadvantage that they are scarcely suitable for active ingredients with an unpleasant taste, that quantitative intake of the intended dose is, as a rule, not ensured, and that they have to be dispersed in an aqueous vehicle, that is to say pure drinking water or a suitable beverage must be available, which in certain areas or, for example, on journeys may make intake difficult or impossible. In addition, the previously disclosed formulations usually have to be mixed with ancillary substances, for example ancillary granules; however, it is known that this may, especially in mixtures of dense particles and granules or micropellets, result in inhomogeneities, which may have an additional adverse effect on use.

Methods for masking the taste of active ingredients with an unpleasant taste are also known to the skilled person from other sources, where, as a rule, the active ingredients are processed to pellets or granules in order to reduce the surface area, and then provided with saliva-resistant coatings.

The present invention is based on the object of providing a novel pharmaceutical formulation for oral administration which ensures quantitative intake of the intended dose, permits intake also of high doses without swallowing difficulties, masks the often unpleasant taste of the active ingredient, and preferably can also be taken without liquid.

The object is achieved according to the invention by a pharmaceutical composition for oral administration, containing at least one pharmaceutical active ingredient in an effective amount and comprising one or more coated particles which have a core containing the at least one pharmaceutical active ingredient, and have a coating consisting of one or more layers, the composition being characterized in that (a) the coating layer or the coating layers contain at least one hydratable, pharmaceutically acceptable polymer which, on contact with saliva or water, forms a coherent, mouldable, viscous mass which is slippery on the surface and does not adhere to the oral mucosa, and which prevents active ingredient-containing particles escaping from the mass, and release of active ingredient in the mouth, and (b) the coating layer or the outermost of the coating layers contains an effective amount of at least one salivation-promoting agent.

Thus, in contrast to the previously disclosed formulations, the composition according to the invention is not dispersed or suspended in an aqueous vehicle before the administration; on the contrary, disintegration of the composition in the mouth or even before administration into individual particles is avoided. This is because it has been found that hydratable polymers rapidly form, in the presence of an adequate flow of saliva, a coherent, mouldable, viscous mass (that is to say a plastic mass) which effectively prevents active ingredient particles escaping and active ingredients being released in the mouth. Since the mass becomes slippery on the surface on contact with saliva, the composition is prevented from adhering to the oral mucosa or to the teeth. Thus, the formation of a mouldable, viscous mass with a slippery surface considerably facilitates the swallowing of the composition—even in the case of high doses—and makes it possible for the composition easily to slide from the mouth through the palate into the oesophagus. In addition, the salivation-promoting agent induces a sufficiently strong flow of saliva for the required effect to be initiated within a few seconds. Even with high doses of up to 10 g, as a rule, an adequately mouldable, coherent, viscous, plastic "particle paste" is formed within less than 20 seconds and allows the composition to be swallowed without difficulties.

The compositions according to the invention can thus, unlike the formulations disclosed in WO-A 91/16043, BR-A 9 403 617, EP-A 0 662 320, U.S. Pat. Nos. 4,882,169 and 5,288,500, be administered by direct administration into the mouth and without previous dispersion in an aqueous vehicle, which prevents particles being able to remain in a vessel or in the mouth. Unlike conventional tablet formulations, they can moreover preferably be taken even without an additional beverage. In addition, the disadvantages of chewable tablets can also be avoided with the formulations according to the invention. This is because children and elderly people in particular often have difficulty in chewing chewable tablets, and the risk of release of active ingredient is increased due to the chewing action and the long residence time in the mouth. Chewing is unnecessary with the formulations according to the invention, and long residence times in the mouth are avoided.

The composition according to the invention can, because of its smooth, slippery surface in the presence of saliva, easily slide from the mouth into the oesophagus and into the stomach and, furthermore, the formation of a coherent, viscous mass ensures that the composition can be completely swallowed, that is to say prevents individual particles remaining in the mouth or between the teeth. Moreover, because of the high surface slip, even relatively large particles, for example a tablet provided with the coating according to the invention and having a maximum diameter of up to 12 mm, can as a rule still be swallowed without problems.

The coating used according to the invention moreover provides a more effective and more reliable masking of the taste than the conventional taste-masking coatings because, as a consequence of the formation of a coherent, viscous mass, it is not damaged even when the coated particles are compressed to tablets and, on the other hand, the high viscosity effectively prevents the active ingredient escaping.

The composition according to the invention can be essentially anhydrous or, as a rule, contain up to about 300% by weight or more water, based on the anhydrous composition, without disintegrating into individual particles or being converted into a dispersion or suspension. The term "essentially anhydrous" means within the scope of the present invention that no water is added to the composition, but that it may contain commercially available polymers and other ancillary substances, which often contain a small percentage of water. For example, commercially available hydratable polymers, which often contain water in amounts of up to about 10% by weight, are suitable even without additional drying. If required, the formulations according to the invention can, however, contain additional water. In particular, an essentially anhydrous composition can be converted by adding about 30 to 300% by weight of water, based on the anhydrous composition, into a soft medicament composition which additionally facilitates the taking of high doses and which has a non-adhesive surface and sufficient consistency for it to be taken, without disintegrating, by hand or, for example, using a spoon or spatula.

The composition according to the invention is suitable in principle for administering any solid active ingredients which have therapeutic and/or prophylactic efficacy and can be administered orally, for example gastrointestinal remedies and digestion-promoting agents such as loperamide, pectin, Plantago ovata seeds, linseeds, mesalazine (5-aminosalicylic acid), olsalazine, cimetidine, ranitidine, famotidine, nizatidine, omeprazole, sucralfate, pantoprazole, metoclopramide, pancreatin, amylase, protease, lipase and sulphasalazine, laxatives such as dry extract of senna pods, frangula bark or extract, bisacodyl, sodium picosulphate and lactulose, analgesics and anti-rheumatics such as acetylsalicylic acid, paracetamol, ibuprofen, morphine, tramadol, acemetacin, propyphenazone, naproxen, diclofenac, ketoprofen, piroxicam, meloxicam and indomethacin, antiallergics such as dimetindene maleate, terfenadine, astemizole and ketotifen, antitussives and expectorants such as ambroxol, acetylcysteine, codeine and theophylline, beta-receptor blockers, calcium channel blockers and ACE inhibitors such as atenolol, metoprolol, pindolol, nifedipine, diltiazem, verapamil, captopril, lisinopril and enalapril, coronary remedies such as isosorbide, isosorbide mononitrate and molsidomine, antiparkinson agents such as levodopa, psychopharmaceuticals such as amitriptyline, trimipramine, thioridazine, oxazepam, lorazepam and piracetam, sedatives such as valerian extract, nitrazepam, temazepam, active ingredients such as aescin, high-dose amino acids, budesonide, furosemide and pentoxifylline, vitamins such as ascorbic acid, vitamin $B_1$, $B_2$, $B_6$ and/or $B_{12}$, folic acid and vitamin E, antibiotics such as ciprofloxacin, norfloxacin, ofloxacin, nalidixic acid, cinoxacin, pefloxacin, phenoxymethylpenicillin, amoxicillin and other penicillins with a penam structure, cephalosporins with a cephem structure such as cefaclor, cefadroxil, cefalexin, cefpodoxime, ceftibuten, cefuroxime and cefetamet, clavulanic acid in combination with amoxicillin, tetracycline, macrolide antibiotics such as erythromycin and its esters, spiramycin and josamycin, colistin and polymyxin B, nitrofurans such as nitrofurantoin, nitroimidazoles such as metronidazole, sulphonamides such as sulphadiazine and sulphasalazine, and the like, and pharmaceutically acceptable salts of such compounds such as, for example, olsalazine sodium, pantoprazole sodium, diclofenac sodium, morphine sulphate, codeine phosphate, metoprolol tartrate, diltiazem hydrochloride, verapamil hydrochloride, amitriptyline hydrochloride, thioridazine hydrochloride and the like. The composition according to the invention is furthermore suitable also for administering mineral salts such as calcium lactate, calcium carbonate, calcium gluconate, magnesium carbonate, magnesium aspartate and zinc sulphate and trace elements. If required, the composition may contain combinations of two or more active ingredients.

Particularly preferred products are those containing as pharmaceutical active ingredient loperamide, mesalazine, olsalazine, cimitidine, ranitidine, famotidine, nizatidine, omeprazole, sucralfate, pantoprazole, pancreatin, bisacodyl, lactulose, acetylsalicylic acid, paracetamol, ibuprofen, morphine, tramadol, naproxen, diclofenac, piroxicam, terfenadine, astemizole, ambroxol, acetylcysteine, theophylline, atenolol, nifedipine, diltiazem, verapamil, isosorbide mononitrate, amitriptyline, nitrazepam, budesonide, ciprofloxacin, norfloxacin, ofloxacin, amoxicillin, cefaclor, cefadroxil, tetracycline, erythromycin, a pharmaceutically acceptable salt of one of these active ingredients or a combination of two or more of these active ingredients and salts.

Suitable salivation-promoting agents are in principle any pharmaceutically acceptable substances which induce a strong flow of saliva, preferably water-soluble organic acids such as tartaric acid, citric acid, malic acid, ascorbic acid and the like, and their water-soluble salts, in particular their sodium and potassium salts such as, for example, sodium or potassium hydrogen tartrate, sodium hydrogen citrate or sodium ascorbate, and water-soluble substances with an osmotic action, such as glucose, fructose, sucrose, xylitol, mannitol, sorbitol, maltitol and the like, it also being possible for the compositions according to the invention advantageously to contain a combination of two or more of these compounds. In a particularly preferred embodiment, the coating layer or the outermost of the coating layers of the composition according to the invention contains as salivation-promoting agent at least one water-soluble organic acid or its water-soluble salt and at least one water-soluble substance with an osmotic action. If required, the coating layer or the outermost of the coating layers may, besides the salivation-promoting agent, contain masking flavours such as sodium chloride, aspartame, saccharin sodium, sodium cyclamate and the like, which generally assist the action of the salivation-promoting agent.

The hydratable polymers suitable according to the invention are those able in the presence of water or saliva to form a coherent viscous mass quickly, preferably within less than about 20 seconds. Suitable natural or semisynthetic polymers are known in principle to the skilled person. Particularly suitable hydratable polymers are those which form highly viscous solutions in water, in particular nonionic polymers with a viscosity, measured as 1% strength (weight/weight) aqueous solution, of from 3 to 10,000 mPa·s, for example polyvinylpyrrolidone and cellulose ethers such as methylcellulose, hydroxyethylcellulose, hydroxypropylcellulose and hydroxypropylmethylcellulose and the like, and ionic polymers with a viscosity, measured as 1% strength (weight/weight) aqueous solution, of from 3 to 30,000 mPa·s, such as sodium carboxymethylcellulose, polyacrylic acids, polyacrylates, alginic acid, alginates, pectin, xanthan, galactomannan, guar gum, hydroxypropyl-guar gum, gelatin, gum arabic and the like, with particular preference generally being given to those with a viscosity, measured as 1% strength (weight/weight) aqueous solution, of at least about 25 mPa·s. It is possible and preferred for the coating of the compositions according to the invention also to contain two or more of these polymers.

The viscosities used within the scope of the present invention relate in each case to the shear viscosity of an aqueous solution at 25° C. The measurements were carried out in each case on a 1% strength (weight/weight) aqueous solution unless expressly indicated otherwise. The measurements were carried out using a rotational viscometer by the following method:

The dried polymer is dissolved in the calculated amount of water by stirring with a mechanical stirrer. The solution is adjusted to a temperature of 25° C.±0.5° C. with a water bath within 30–60 minutes. The solution is then shaken for about 10 seconds, and the viscosity is immediately measured using a Brookfield viscometer (Brookfield Synchro-Lectric Model LVF with four speeds and four spindles and a measurement range from 0 to 100,000 mPa·s), allowing the spindles of the viscometer to run for exactly 3 minutes in each case, reading off the value, and calculating the viscosity of the solution by multiplying the latter by the fixed factor for the chosen speed.

Examples of particularly preferred hydratable polymers are: alginic acid or alginates, for example sodium alginate, with a viscosity of from 25 to 2000 mPa·s, a pH of about 7 and a molecular weight of about 200,000; pectin with a viscosity of from 50 to 5000 mPa·s, a pH of from 3.8 to 5.2 and a molecular weight of about 100,000; xanthan with a viscosity of from 25 to 3000 mPa·s, a pH of about 6 and a molecular weight of more than 1,000,000; galactomannan with a viscosity of from 50 to 1000 mPa·s, a pH of from 4 to 8 and a molecular weight of about 200,000; gelatin (type A or B) with a viscosity of from 5 to 200 mPa·s, a pH of from 4 to 9 and a molecular weight of from 10,000 to 100,000; sodium carboxymethylcellulose with a viscosity of from 25 to 8000 mPa·s, preferably 2500 to 8000 mPa·s, with a degree of polymerization of from 500 to 2000 and with a degree of substitution not exceeding 3, that is to say not exceeding 3, preferably 0.45 to 1.45 and particularly preferably 0.65 to 0.95 carboxymethyl groups per anhydroglucose unit; cellulose ethers with a viscosity of from 3 to 10,000 mPa·s, a degree of polymerization of from 40 to 2000 and a degree of substitution not exceeding 3, in particular hydroxyethylcellulose with a viscosity of from 3 to 10,000 mPa·s, preferably 25 to 7000 mPa·s, and a degree of substitution of about 2.5, hydroxypropylcellulose with a viscosity of from 10 to 5000 mPa·s and a molecular weight of from 80,000 to 1,300,000 and methylhydroxypropylcellulose with a viscosity of from 3 to 10,000 mPa·s, with a degree of substitution of from 1 to 2 and, preferably, a methoxyl content of from 18 to 32% and a hydroxypropoxyl content of from 7 to 15%; polyvinylpyrrolidone with a molecular weight of from 17,000 to 90,000; polyacrylic acids and polyacrylates with a molecular weight of from 400,000 to 4,000,000 and, for example, a viscosity of about 30,000 mPa·s; where the viscosity and pH values in each case relate to a 1% strength aqueous solution.

Whereas some of the hydratable polymers, for example polyvinylpyrrolidone or cellulose ethers, have a substantially pH-independent viscosity, a large decline in viscosity occurs in the pH range of the gastric fluid with others, for example with sodium carboxymethylcellulose, sodium alginate or polyacrylic acids. This difference can therefore be utilized to influence specifically the disintegration of the composition in the stomach. If, for example, sodium carboxymethylcellulose, sodium alginate or a polyacrylic acid is used as hydratable polymer, on the one hand the required high viscosity in the mouth is achieved but, on the other hand, the composition rapidly disintegrates in the stomach and thus permits rapid release of active ingredient.

The hydratable polymers preferably have an average particle size not exceeding about 1.0 mm, typically about 0.01 to 1.0 mm. If it is particularly important that a coherent, viscous mass is formed as rapidly and uniformly as possible, preferably a small particle size is chosen. As a rule, therefore, hydratable polymers with an average particle size not exceeding 200/$\mu$m, in particular not exceeding 100 $\mu$m, are preferably used.

The compositions according to the invention can, if required, have two or more coating layers each containing at least one hydratable polymer. In a preferred embodiment of the present invention, the coating can consist of two or more layers which are characterized in that the viscosity, measured as 1% strength (weight/weight) aqueous solution, of the hydratable polymer in a layer is in each case not larger, and may preferably be smaller, than the viscosity, measured as 1% strength (weight/weight) aqueous solution, of the hydratable polymer in the adjacent inner layer of the coating. It is possible in this way additionally to improve the taste-masking properties and, nevertheless, ensure rapid penetration in of the saliva, because the saliva is able quickly to penetrate into the outermost layer and thus a coherent, viscous mass with a slippery surface is rapidly formed, whereas although the inner layer or the inner layers react more slowly with saliva they do produce a high-viscosity mucilage and thus form an extremely effective barrier to release of active ingredient, which is particularly advantageous in the case of active ingredients with an unpleasant taste.

For this purpose, it is possible and preferred for the outermost layer to contain a hydratable polymer with a viscosity of from 25 to 5000 mPa·s, and the second outermost layer a nonionic, hydratable polymer with a viscosity of from 5000 to 10,000 mPa·s and/or an ionic polymer with a viscosity of from 5000 to 30,000 mPa·s, the viscosities in each case being based on a 1% strength (weight/weight) aqueous solution of the polymer.

In order to ensure maximum masking of the taste, it is preferred to use in the second outermost layer and in any other inner layers of the coating a hydratable polymer with an average particle size not exceeding 50 $\mu$m, for example 10–25 $\mu$m. The average particle size of the hydratable polymer in the outermost layer is less critical, but is preferably not more than about 200 $\mu$m.

Suitable in principle for the coatings consisting of two or more layers are all the abovementioned hydratable polymers as long as they have the required viscosity. However, it is possible and preferred to use in the outermost layer a polymer which allows the viscosity to be built up as pH-independently as possible. Examples of hydratable polymers which have proved to be particularly suitable for the second outermost and any other inner layers of the coating are sodium carboxymethylcellulose with a viscosity of from 5000 to 8000 mPa·s, polyacrylic acid with a viscosity of from 5000 to 30,000 mPa·s and cellulose ethers with a viscosity of from 5000 to 10,000 mPa·s, whereas nonionic hydratable polymers have proved to be particularly suitable for the outermost coating layer, in particular polyvinylpyrrolidone and cellulose ethers with a viscosity of from 25 to 5000 mPa·s (where the viscosities are in each case based on a 1% strength (weight/weight) aqueous solution of the polymer).

If required, the coating can also consist of a single layer in which at least one of each of the hydratable polymers indicated above for the outermost and the second outermost layer are present in a mixture. It is possible in this way to achieve similar advantages, but to a smaller extent.

The coating layer or coating layers can in each case contain one or more hydratable polymers, if required vicosity-regulating ancillary substances such as silicon dioxide and, furthermore, other conventional ancillary substances, for example odorizers, flavours, sweeteners, pH-regulating ancillary substances, pore-forming ancillary substances such as alkali metal or alkaline earth metal carbonates or bicarbonates, surface-active ancillary substances, tabletting ancillary substances such as microcrystalline cellulose, corn starch, tablet disintegrants and lubricants (for example stearic acid or magnesium stearate) and other ancillary substances such as starch, crospovidone, croscarmelose, talc and the like, with tabletting ancillary substances and odorizers, flavours and sweeteners as a rule being employed only in the outermost layer whereas, on the other hand, the second outermost layer and any other inner layers may contain preferably a viscosity-regulating ancillary substance such as silicon dioxide and/or a basicity-increasing ancillary substance such as sodium bicarbonate or sodium carbonate.

The proportion of hydratable polymer in the coating layers may vary within certain limits depending on the polymer used, the use of viscosity-regulating ancillary substances, the required administration form and the like; however, it must in every case be sufficient for a coherent, viscous mass to be formed on contact with saliva or water. The optimal amounts can easily be determined from case to case by adding water or saliva. It is possible typically for the amount of hydratable polymer in the second outermost layer to be about 0.25 to 35% by weight, calculated as essentially anhydrous polymer and based on the essentially anhydrous active ingredient-containing core, and in the outermost layer to be about 1 to 30% by weight, calculated as essentially anhydrous polymer and based on the essentially anhydrous complete composition.

The proportion of the coating layer or coating layers in the compositions according to the invention can preferably be about 5 to 75% by weight based on the essentially anhydrous composition, equivalent to about 5 to 300% by weight of essentially anhydrous coating based on the active ingredient-containing core. If the coating consists of two or more layers, the proportion of the second outermost layer can typically be about 0.25 to 50% by weight, in particular about 0.5 to 20% by weight, and particularly preferably about 1 to 10% by weight, calculated as essentially anhydrous layer and based on the essentially anhydrous active ingredient-containing core, and the proportion of the outermost layer can typically be about 3 to 60% by weight, calculated as essentially anhydrous layer and based on the essentially anhydrous composition.

The coated particles can typically have a maximum diameter of about 0.25 to 12 mm and be, for example, granules, pellets or tablets provided with the coating according to the invention. Depending on the required mode of administration, these coated particles can be either administered directly or further processed in a manner known per se with conventional ancillary substances to give other oral administration forms. For example, coated pellets or granules can be compressed with conventional tabletting ancillary substances to tablets which contain several or a large number of coated particles. It is furthermore possible and preferred for pellets or granules provided with one or more inner coating layers to be enveloped in an outer coating layer according to the invention by mixing with the outer coating material and, for example, by compression to a tablet, that is to say for there to be formation of a tablet which contains several coated particles and in which the outermost coating layer simultaneously serves as tabletting aid. In the case of compositions which consist of several coated particles—irrespective of whether these are in the form of pellets or granules or are contained in a tablet—on contact with saliva there is in each case rapid formation of a viscous mass which causes the particles to stick together. In addition, the composition according to the invention may, for example, be designed as a tablet in which the coating layer or the outermost of the coating layers has not been applied to the active ingredient-containing particle but envelopes the latter in the form of a press-coated tablet. Suitable administration forms and suitable methods for further processing are familiar in principle to the skilled person.

It is furthermore possible for the composition according to the invention to consist, for example, of a single coated particle with a maximum diameter of about 3 to 12 mm and to be, for example, a tablet provided with the coating according to the invention, because the high surface slip of the coating also allows particles with a maximum diameter of more than 7 mm to be swallowed without problems; it is possible and preferred in this case for the coating to consist of at least two layers.

In another preferred administration form it is possible for essentially anhydrous compositions according to the invention to be mixed with a metered amount of about 30 to 300% by weight, for example about 100% by weight, of water based on the anhydrous composition, in which case the water is absorbed within a few seconds, and there is formation of a single, coherent, viscous mass with sufficient consistency to allow it to be taken, without disintegrating and without problems by hand or using a spoon or spatula. The resulting "soft" formulation thus has a water content of about 23 to 75% by weight, for example 50% by weight, based on the hydrous composition, and it has a non-adhesive surface. This mode of administration is particularly suitable for taking several coated particles, for example for taking a metered amount of coated pellets or granules or for taking a tablet containing several coated particles, and it makes it possible in particular to take very large amounts of up to 10 g and more without swallowing difficulties arising or there being the risk that active ingredient-containing particles remain in mouth.

The present invention likewise relates to a process for producing the novel pharmaceutical composition, which is characterized in that one or more particles containing at least one pharmaceutical active ingredient in an effective amount are coated with one or more layers, where
    (a) the layer or layers contain at least one hydratable, pharmaceutically acceptable polymer which on contact with saliva or water forms a coherent, mouldable, viscous mass which is slippery on the surface and does not adhere to the oral mucosa, and which prevents active ingredient particles escaping from the mass and active ingredient being released in the mouth, and (b) the layer or the outermost layer contains an effective amount of at least one salivation-promoting agent, in that, if required, the coated particles are converted with pharmaceutical ancillary substances into a pharmaceutical presentation, and in that, if required, the composition is mixed with water in an amount of up to about 300% by weight, based on the essentially anhydrous composition.

The application of the coating layers to the active ingredient-containing particles can take place in a manner known per se by conventional methods, for example by alternate moistening and coating with a powder mixture in a spheronizer or by spraying on a solution or suspension of the coating materials. These and other suitable methods are very familiar to the skilled person. If water is added to the essentially anhydrous composition, this can in principle take place in any amounts up to about 300% by weight; however, it is possible and preferred to add about 30 to 300% by weight, based on the essentially anhydrous composition, in order to obtain the abovementioned "soft" formulation.

The active ingredient-containing cores used according to the invention can likewise be obtained in a manner known per se by conventional methods. If required, the core may contain pH-regulating additives or be coated with a taste-masking coating layer which is resistant to the gastric fluid or delays release of the active ingredient. Suitable materials and methods are well known to the skilled person.

The present invention likewise relates to a medicinal product pack comprising a pharmaceutical composition according to the invention and the instructions that the composition be taken by direct administration into the mouth or, before intake, be mixed with an amount of from 30 to 300% by weight of water, based on the essentially anhydrous pharmaceutical composition.

The invention further relates to a method for treating or preventing diseases by oral administration of a pharmaceutical composition, comprising the production of the composition according to the invention, if required the addition of a metered amount of from 30 to 300% by weight of water, based on the composition, and direct administration into the mouth, it also being possible and preferred for the composition to be taken without taking any liquid.

The present invention furthermore relates to the coherent, viscous composition formed on exposure to saliva, that is to say a pharmaceutical composition for oral administration, comprising one or more particles which contain at least one pharmaceutical active ingredient in an effective amount, and a coherent, viscous mass which is formed on contact with saliva, is slippery on the surface and does not adhere to the oral mucosa, which envelopes the active ingredient-containing particle or the active ingredient-containing particles, which prevents active ingredient-containing particles escaping from the mass and active ingredient being released in the mouth, and facilitates swallowing of the composition, and which contains an effective amount of at least one salivation-promoting agent and at least one hydratable, pharmaceutically acceptable polymer in at least partially hydrated form.

Further preferred aspects of the composition according to the invention and its production and administration are evident from the following explanations and the examples.

To produce the compositions according to the invention, the active ingredients are processed with generally customary ancillary substances to granules, pellets, round or oblong tablet cores etc. with a diameter of, typically, about 0.1 to 10 mm. These active ingredient-containing particles can be produced in a manner known per se.

To produce granules, for example, the active ingredient is mixed with ancillary substances such as microcrystalline cellulose or lactose, and the homogeneous mass is moistened with a binder solution. After the moistening, the granules are sieved and dried, and a dust-free fraction of particles with a diameter of, for example, from 0.1 to 2.5 mm, preferably 0.25 to 1.5 mm, is sieved off.

Pellets can be produced by employing all conventional pellet production processes. These frequently start from starter cores. These can be, for example, sugar beads rounded off with starch, spheroidal crystals such as sucrose, tartaric acid, citric acid or the like, low-cost and physiologically acceptable ancillary substances, and typically have a diameter of from 0.1 to 2 mm, preferably 0.4 to 1.0 mm. After the moistening with an adhesive solution, the active ingredient is applied as powder or in dissolved or suspended form to the starter cores. In the case of active ingredient solutions or suspensions, the coating of the starter cores can advantageously take place in a fluidized bed process by continuously spraying the particles with the active ingredient solution or suspension. In the case of powder coating, the starter cores are expediently loaded by alternate moistening with adhesive solution and application of the active ingredient powder. It is possible, if required, to add ancillary substances such as binders, silicon dioxide or talc to the active ingredient powder in order to optimize the rounding process. If required, the adhesive solution may also be a coating solution or an emulsion which slows release or is resistant to gastric fluid in order to influence the release of the active ingredient from the loaded pellets. It is also possible if required to add to the active ingredient powder mixtures pH-regulating, acidic or basic ancillary substances which, through producing a corresponding micromilieu, influence the dissolution of the active ingredient. Suitable materials and methods are well known to the skilled person.

The pellets can preferably be produced in a so-called spheronizer. This entails the starter cores being introduced into a vessel which is equipped with a rotating base plate and in which they are sprayed on one side with an adhesive or polymer solution and are dusted on the opposite side with the active ingredient powder via a weigh feeder. It is possible in this way to double the weight by loading with powder within one hour in a continuous process, it normally being possible to apply up to about 6 parts of active ingredient powder to 1 part of starter cores.

Another method suitable for the compositions according to the invention is based on extrusion and spheronization. This entails the active ingredients being mixed with plasticizing ancillary substances, moistened and extruded. The extrudate with a diameter of, typically, about 0.4 to 2 mm is transferred into the spheronizer where it breaks up into cylindrical particles which are rounded to beads under the influence of the centrifugal force. If required, the release characteristics of the active ingredient pellets can be influenced in a known manner with polymer solutions, release-slowing, solubilizing or pH-regulating ancillary substances etc.

It is furthermore possible, if required, for active ingredient granules to be compressed isostatically by known methods in rubber dies to particles of about 1 mm or to be tabletted with special punches to round or oblong particles about 1 to 10 mm in size.

The resulting active ingredient-containing particles can if required, before the enveloping with the coating according to the invention, be coated, by spraying with coating polymer solutions in a manner known per se, with diffusion membranes, eroding membranes and/or membranes resistant to gastric fluid, whereby the release characteristics of the compositions according to the invention can be varied within wide limits and, where appropriate, additional masking of the taste can be achieved.

The active ingredient-containing particles, which may preferably have a maximum diameter of about 0.1 to 10 mm, particularly preferably about 0.25 to 1.5 mm, are subsequently coated with one or more layers containing a hydratable polymer. The application of the layer or layers can take place by conventional methods and with conventional equipment well known to the skilled person. Preferred methods and possible applications are illustrated in the examples and are explained in detail hereinafter by means of some exemplary formulations and administration forms.

In the case of loperamide, which has a very bitter taste and which the patient with severe diarrhoea ought to be able to take anywhere even without water, it is possible to obtain a formulation according to the invention for example by compressing loperamide with conventional ancillary substances to a compact to about 5 mm in size, and coating the compact in a coating apparatus with a suspension of sodium alginate and polyvinylpyrrolidone K 90, in which case it is possible to apply, for example, about 8% by weight of polymers, based on the weight of the compact. Subsequently, the coated compact is coated with an outer polymer layer consisting of a low-viscosity polymer, citric acid, aspartame and lemon flavour.

As a rule, travellers in tropical countries do not have access to microbiologically satisfactory water for taking a loperamide tablet or capsule if severe diarrhoea occurs. However, when the described formulation according to the invention is taken, the outer polymer layer causes a spontaneous flow of saliva in a sufficient amount which makes it straightforwardly possible to swallow the loperamide compact, which is enveloped by the high-viscosity gel layer, even without the aid of water. Since the viscosity of sodium alginate decreases greatly at low pH, the tablet disintegrates in the stomach, and the active ingredient is rapidly released.

In the case of active ingredients with an extremely unpleasant bitter taste, such as, for example, ciprofloxacin, it is possible, for example, to provide active ingredient granules or pellets initially with a taste-masking coating. For this purpose, the particles can be coated for example in a known manner with coatings which are resistant to gastric fluid or resistant to saliva, or preferably be enveloped with a hydratable, high-viscosity, inner polymer layer according to the present invention. A particularly suitable hydratable polymer is micronized sodium carboxymethylcellulose of maximum viscosity with an average particle size of about 10 to 25 $\mu$m, which can, for example, be applied as polymer powder to the active ingredient particles which have been moistened with an alcohol/water mixture, or be sprayed as suspension in an alcoholic solvent onto the particles. This achieves in a simple manner a very uniform distribution of the polymer on the active ingredient particles, which is important for perfect resistance to saliva. It is possible, depending on the required rate of release of active ingredient, to apply for example about 0.5 to 20% by weight, preferably about 1 to 10% by weight, of polymer, based on the weight of the active ingredient particles. The coated active ingredient particles are subsequently coated with an outer polymer layer which contains at least one low-viscosity, hydratable polymer, at least one salivation-promoting agent and, where appropriate, ancillary substances such as sweeteners, flavours, pH-regulating, pore-forming or surface-active ancillary substances and/or tabletting ancillary substances, which facilitate the penetration of the saliva into the inner polymer layer. The outer polymer layer can preferably be applied in an amount of about 5 to 150% by weight, based on the weight of the active ingredient particles provided with the inner coating.

The nature and amount of the hydratable polymer employed depends to a certain extent on the required mode of administration. If, for example, coated granules or pellets are administered directly into the mouth, for example with the aid of a spoon, it is important that the particles are stuck together by the polymer within a few seconds to give a consistent, coherent, soft "particle paste", it being necessary, especially with active ingredients with an extremely bitter taste, to avoid the possibility of particles remaining in the mouth. It is possible in this way to swallow amounts of, for example, 3 to 4 g or, if necessary, even amounts of up to about 10 g quantitatively and without problems. By contrast, if it is attempted to swallow conventional slow-release pellets in such amounts, it is unavoidable that some pellets get between the teeth or into the cheek pouches so that there is the risk that active ingredient is gradually released in the mouth, or the masking of the taste is destroyed by chewing movements.

In another very advantageous administration form, pellets or granules according to the invention can be packed in a pellet dispenser from which metered amounts can be dispensed into a small cup, or packed in thermoformed recesses and closed with a sheet. Suitable pellet dispensers and packaging materials are well known to the skilled person. Before administration, the particles according to the invention in the cup or recess have a metered amount of water poured over them, for example with the aid of a measuring spoon which is also supplied, in which case the particles absorb the added water within a few seconds and are converted into a soft, consistent, coherent mass which envelopes the active ingredient particles and does not adhere to the walls of the cup or recess. In this case, the formulation as a rule maintains, on addition of amounts of up to 300% by weight of water, based on the weight of the coated particles, sufficient consistency for it to be taken quantitatively by hand or with the aid of a spatula or spoon. If this hydrated formulation is applied to the tongue, it can be swallowed very easily—assisted by the salivation which occurs.

A great advantage of this administration form is that virtually any required amount of active ingredient can be administered in this way. For example, amounts of up to 10 g with an active ingredient content of up to about 5 g can be swallowed without any type of swallowing difficulties occurring. In addition, the mass can easily be moulded by the tongue, with exposure to saliva, into smaller lumps which can be swallowed, so that even larger amounts can be taken without problems if required. This administration form has the further advantage that the coated active ingredient particles are stuck together even before intake, and diffusion of active ingredient particles away in the mouth is precluded from the outset.

Particles coated according to the invention, such as pellets or granules, can also be processed further to tablets. For this purpose, the particles can be mixed with conventional tabletting ancillary substances and compressed to tablets in a manner known per se. However, it is possible and preferred for any tabletting ancillary substances to be present in the coating of the particles and for the coated particles to be compressed direct to tablets, without adding further ancillary substances, whereby any inhomogeneity of the mixture of ancillary substances and particles is precluded. Tablets which contain a large number of coated particles are therefore produced preferably by using particles such as pellets or granules which have a coating consisting of at least two layers and which may contain in the outermost coating layer besides at least one hydratable polymer, at least one salivation-promoting agent and any ancillary substances, such as sweeteners and flavours, preferably also one or more tabletting ancillary substances such as microcrystalline cellulose and, if necessary, further ancillary substances which facilitate the penetration of saliva, such as starch, crospovidone, croscarmelose and silicon dioxide. Even a low pressure moulds these particles to a tablet which holds together well and, as a consequence of the easy deformability of the outermost layer, the taste-masking effect of the inner layer or inner layers is not destroyed. On administration into the mouth there is immediately pronounced salivation, and the saliva penetrates rapidly into the tablet and converts it into a soft, coherent "particle paste" which can be moulded with the tongue.

As already illustrated above by means of the loperamide formulation, the composition according to the invention can also consist of a single coated particle and, for example, be a tablet provided with the coating according to the invention. In these cases it is generally preferred to use a coating consisting of at least two layers and having the properties explained above. It is also possible and preferred for a formulation of this type to be obtained not by applying the outermost layer to the particle but by enveloping the latter in the form of a press-coated tablet.

The invention is illustrated further by the following examples. Viscosity data relate in each case to a 1% strength aqueous solution. Percentage data refer in each case to % by weight unless expressly indicated otherwise. The hydratable polymers and ancillary substances used in the examples were commercially available materials such as polyvinylpyrrolidone K 25 or polyvinylpyrrolidone K 90 (BASF, Ludwigshafen/FRG), crospovidone or Polyplasdone (crosslinked polyvinylpyrrolidone; BASF, Ludwigshafen/FRG or ISP/FRG), croscarmelose (crosslinked sodium carboxymethylcellulose; FMC, Brussels/Belgium), Blanose 7H4 or Blanose 7H9 (sodium carboxymethylcellulose; Aqualon, Dusseldorf/FRG), Culminal (methylcellulose; Hercules, Milldate/USA), Natrosol 250 HHX (hydroxyethylcelllulose; cellulose; Aqualon, Dusseldorf/FRG), hydroxypropylcellulose LH 11 or hydroxypropylcellulose LH 20 (Shinetsu, Tokyo/Japan), Klucel L (hydroxypropylcellulose; Shinetsu, Tokyo/Japan), Metolose 60 SH-50 (hydroxypropylmethylcellulose; Shinetsu, Tokyo/Japan), Pharmacoat (hydroxypropylmethylcellulose; Shinetsu, Tokyo/Japan), Tablettose (lactose; Meggle, Wasserburg/FRG), Eudragit L or Eudragit S coating (methacrylic acid polymer type A or B; Röhm, Darmstadt/FRG) and Eudragit RS coating (ammonium methacrylate copolymer type B; Röhm, Darmstadt/FRG).

EXAMPLE 1

Production of the Active Ingredient Core:

| Ciprofloxacin base, micronized, or Ciprofloxacin hydrochloride | 2000 g |
| Crospovidone XL-M (Polyplasdone XL-M) | 110 g |
| Polyvinylpyrrolidone K 90 | 60 g |
| Water | 900 g |
| Ethanol | 1800 g |

Polyvinylpyrrolidone is dissolved in the mixture of ethanol and water; the remaining powders are then stirred into the solution under high shear. The 44.6% strength suspension is sprayed in a fluidized bed apparatus at an inlet air temperature of 40° C. onto 1.5 kg of sieved sucrose crystals with a diameter of from 0.3 to 0.6 mm. The dried and sieved particles (diameter 0.5–1.0 mm) contain about 54% of active ingredient.

Application of the Polymer Layer:

The particles are coated in portions, in each case after previous moistening, in a spheronizer with a powdered mixture of 50 g of sodium chloride (milled), 50 g of saccharin sodium (milled) and 50 g of sodium carboxymethylstarch.

The particles are then coated, in each case after moistening with ethanol/water 1:1, with a powdered mixture of 275 g of sodium carboxymethylcellulose (Blanose 7H9, 8000 mPa·s) and 75 g of talc.

EXAMPLE 2

88 parts by weight of the pellets obtained in Example 1 were coated in the spheronizer, in each case after previous moistening with a 10% strength ethanolic solution of polyvinylpyrrolidone K 25, with 12 parts by weight of a mixture of

| Mannitol | 4 parts |
| Xanthan powder (3000 mPa · s, MW 1,000,000) | 4 parts |
| Monosodium citrate | 3 parts |
| Sodium cyclamate/saccharin sodium 9:1 | 0.25 part |
| Lemon flavour powder | 0.25 part |
| Silicon dioxide | 0.5 part |

(stated amounts of the components in parts by weight).

The pellets were then coated, to improve the mechanical stability, with 0.5% by weight (based on the pellets employed) of hydroxypropylmethylcellulose, by means of a solution containing 6% by weight of hydroxypropylmethylcellulose in ethanol/water 9:1.

Addition of water or saliva to these pellets results in almost instantaneous formation of an adhesive, viscous layer around the pellets, which on the one hand prevents diffusion of the active ingredient, which has an extremely bitter taste, into the mouth for at least 3–5 minutes, and on the other hand causes the metered pellets to adhere together to give a coherent, soft, deformable particle paste.

EXAMPLE 3

A plasticized mass containing 80% by weight of active ingredient is produced from ciprofloxacin hydrochloride, microcrystalline cellulose, polyethylene glycol 6000 and hydroxypropylcellulose LH 20 (Shin-Etsu, Japan) in a manner known per se and converted by extrusion and spheronization into pellets with a diameter of 0.6–1.25 mm. 3 kg of these pellets are coated in the spheronizer, in each case after previous moistening with a 10% strength ethanolic polyvinylpyrrolidone solution, with 150 g of ground sodium carbonate. The pellets are then coated in a film-coating system by spraying with an 8% strength ethanolic solution with 50 g of ethylcellulose (7 mpa·s) and 25 g of talc.

The resulting pellets are resistant to saliva for at least 5 minutes, and virtually no bitter taste is detected in the mouth during this period.

3.1 kg of the resulting pellets are sprayed in a spheronizer using a two-component nozzle with a 25% strength ethanolic suspension of 70 g of micronized sodium carboxymethylcellulose (Blanose 7H4, 8000 mPa·s, average particle size 20 μm) and 23 g of hydroxypropylmethylcellulose (Metolose 60 SH-50, 25 mPa·s).

3.15 kg of the resulting coated pellets are coated in the spheronizer, in each case after previous moistening with ethanol/water 1:1, with a powdered mixture of

| | |
|---|---|
| α-Lactose monohydrate (200 mesh) | 200 g |
| Hydroxyethylcellulose (Natrosol 250 HHX, 3000 mPa · s) | 200 g |
| Monosodium citrate (powder) | 100 g |
| Sodium cyclamate/saccharin sodium 9:1 | 12 g |
| Dry apple flavour | 11 g |
| Silicon dioxide | 4 g |
| Hydroxypropylcellulose LH 11 | 15 g |

Before the drying and sieving, the pellets are also coated with a 6% strength hydroxypropylmethylcellulose solution (ethanol/water 8:2) until the weight gain is 0.5%. 98% of the particles have a maximum diameter between 0.8 and 1.6 mm; the active ingredient content is 54%.

EXAMPLE 4

926 mg of pellets from Example 3 are packed into a hard gelatin capsule of size 000 (without closure groove). After the capsule has been opened by pulling off the capsule cap, the particles according to the invention are emptied onto a teaspoon. Application of these particles to the tongue by means of the spoon results in spontaneous salivation which causes the particles to stick together within a few seconds to give a pleasant-tasting particle paste. The gelatinous paste does not adhere either to the tongue or to the teeth and can easily be swallowed.

Addition of about 1 ml of water to the particles on the spoon causes the pellets to merge within 10 seconds to a viscous, coherent paste which is not sticky on the surface. This particle paste is very easy to swallow without particles remaining in the mouth.

EXAMPLE 5

1.85 g portions of the ciprofloxacin particles obtained in Example 3 are placed in round, thermoformed PVC recesses (initial PVC sheet 250 μm), and the recesses are sealed with a peel-off sheet. For administration, the peel-off sheet is pulled off and an applicator spoon is used to put 2 g of water in the thermoformed recess with the pellets. The water is immediately absorbed, and the pellets according to the invention are converted within 10 seconds into a viscous, coherent pellet paste which is not sticky on the surface. The spatula part of the applicator can be used to remove the coherent paste quantitatively from the recess. The particle paste is gelatinous on the surface and can easily be swallowed quantitatively without particles remaining in the mouth.

EXAMPLE 6

1.85 g portions of the ciprofloxacin particles obtained in Example 3 are placed in round, thermoformed, biplanar recesses (diameter 20 mm, depth about 10 mm), and the recesses are sealed with peel-off sheet. The initial PVC sheet has a thickness of 150–200 μm. For administration, the peel-off sheet is pulled off and the applicator is used to put 1.5 g of water on the ciprofloxacin particles. The water is immediately absorbed, and the pellets according to the invention form within 30 seconds a viscous, coherent, biplanar pellet paste tablet. Pressure from below on the flexible recess allows the pellet paste tablet to be expelled quantitatively. It is gelatinous and non-sticky on the surface and it can be picked up in the fingers and placed in the mouth. The salivation which starts makes it possible to mould the tablet with the tongue to one or two elongate paste lumps which can easily be swallowed.

EXAMPLE 7

Ciprofloxacin pellets from Example 2 are packed in a pellet dispenser which, when the metering head is turned once, dispenses about 1.85 g of pellets into an attached cup. As described in Example 5, a metered amount of water can be put, using an applicator, into the cup and the viscous coherent pellet paste which forms can be removed quantitatively with a round-shaped spatula.

EXAMPLE 8

Loperamide-containing particles are produced using the following components:

| | | per particle |
|---|---|---|
| Loperamide | 0.2 kg | 2 mg |
| Lactose | 5.0 kg | 50 mg |
| Polyvinylpyrrolidone | 0.2 kg | 2 mg |
| Microcrystalline cellulose | 1.0 kg | 10 mg |
| Corn starch | 0.6 kg | 6 mg | with the micronized active ingredient and the ancillary substances being mixed and moistened with water, and the moistened mass being forced through a 2.0 mm sieve. After drying and sieving through a 0.8 mm sieve, 4.5 mg of crospovidone and 0.5 mg of magnesium stearate are added per particle, and the mixture is compressed to biconvex particles with a diameter of 5 mm.

400 g of sodium alginate (2000 mpa·s, average particle size 15 μm) and 50 g of polyvinylpyrrolidone K 90 are sprayed as solution or suspension in 1.2 kg of isopropanol onto 6.0 kg of the resulting particles (80,000 particles). An outer coating layer is then applied to the coated particles by spraying the particles with a suspension of 820 g of citric acid, 160 g of saccharin sodium, 25 g of liquid lemon flavour, 150 g of hydroxypropylcellulose (Klucel L, 20 mPa·s), 250 g of talc and 2645 g of ethanol (75% strength).

In the mouth, the particles produce almost instantaneously considerable salivation with which it is possible to swallow, without further water, the particle which is enveloped by a viscous, coherent layer. The bitter taste of loperamide does not appear.

EXAMPLE 9

3 kg of lactose granule particles (Tablettose, 0.3–0.6 mm) are coated in a coating apparatus with a solution of 75 g of loperamide, 75 g of saccharin sodium, 150 g of sodium chloride, 200 g of water and 800 g of ethanol.

The resulting particles are coated in a spheronizer, in each case after previous moistening with 10% strength ethanolic polyvinylpyrrolidone solution, with a mixture of 235 g of xanthan powder (3000 mPa·s) and 50 g of talc and then with a mixture of 1.5 kg of microcrystalline cellulose, 0.2 kg of citric acid (powder), 0.1 kg of aspartame, 0.1 kg of dry orange flavour and 150 g of methylcellulose (Culminal, 3000 mPa·s).

The dried particles are compressed to biplanar tablets with a weight of 150 mg (diameter 8 mm). In the mouth, as a consequence of the stimulated salivation, the tablets produce within 20 seconds a coherent, soft, viscous particle paste which can be swallowed very easily without water. The bitter taste of loperamide is undetectable.

EXAMPLE 10

3.0 kg of ciprofloxacin hydrochloride particles coated with a layer of sodium carboxymethylcellulose and hydroxypropylmethylcellulose (without salivation-promoting outer layer) are produced as in Example 3 and, in each case after previous moistening with a 10% strength ethanolic polyvinylpyrrolidone solution (1.3 kg of solution used), a mixture of 1.7 kg of microcrystalline cellulose, 0.3 kg of sodium carboxymethylstarch, 0.15 kg of citric acid, 0.4 kg of hydroxpropylmethylcellulose (7.5 mPa·s), 0.05 kg of aspartame and 0.1 kg of dry lemon flavour powder is applied in portions. After drying the particles have a content of about 33% by weight of ciprofloxacin hydrochloride.

Biplanar tablets with a diameter of 20 mm and an active ingredient content of 750 mg of ciprofloxacin hydrochloride are compressed from these particles under low pressure after admixing 0.5% by weight of magnesium stearate. The hardness of the tablets is about 60 N. When a tablet is placed on the tongue, the salivation which starts causes within 20 seconds the formation of a coherent, viscous particle paste which does not adhere to the tongue, the pallet and the teeth and can easily be swallowed.

EXAMPLE 11

3 kg of pellets which have been produced in a manner known per se, are resistant to gastric fluid and have an active ingredient content of 73% by weight of 5-aminosalicylic acid are coated in a spheronizer, in each case after previous spraying with a 10% strength polyvinylpyrrolidone solution in ethanol/water 7:3, with a powdered mixture of 100 g of sodium carboxymethylcellulose (Blanose 7H4, 8000 mPa·s, average particle size 20 μm), 25 g of monosodium citrate, 15 g of aspartame and 30 g of dry vanillin powder.

The dried and sieved particles (0.8–1.4 mm) are packed in a pellet dispenser which dispenses 1450 mg of pellets, equivalent to 1000 mg of 5-aminosalicylic acid, by twisting the metering head. When the pellets are placed on the tongue using a spoon, they produce within 10 seconds a soft, coherent pellet paste which can easily be swallowed.

EXAMPLE 12

3 kg of pellets which have been produced in a manner known per se, are resistant to gastric fluid and have an active ingredient content of 73% by weight of 5-aminosalicylic acid are coated in a spheronizer, in each case after previous spraying with a 10% strength ethanolic polyvinylpyrrolidone solution, in portions with a powdered mixture of 1.6 kg of microcrystalline cellulose, 0.3 kg of sodium carboxymethylstarch, 0.3 kg of adipic acid, 0.13 kg of sodium bicarbonate, 0.15 kg of hydroxypropylmethylcellulose (Pharmacoat, 25 mPa·s), 0.12 kg of aspartame and 0.11 kg of dry vanillin powder and 0.1 kg of silicon dioxide.

1.5 kg of polyvinylpyrrolidone solution are required for the coating. After drying, the particles have an active ingredient content of about 35% by weight. Biplanar tablets with a diameter of 23 mm and a weight of 2860 mg, equivalent to 1000 mg of active ingredient, are compressed from these particles under low pressure. The hardness of the tablets is 60–80 N. The tablets produce increased salivation in the mouth and form within 20 seconds a coherent, soft pellet paste which can easily be deformed with the tongue and is easy to swallow.

EXAMPLE 13

Active ingredient pellets with an amoxicillin content of 68% by weight are produced from amoxicillin, microcrystalline cellulose, hydroxypropylcellulose and lactose by known processes of extrusion and spheronization. Some of these pellets are converted in a known manner, by coating with Eudragit L and Eudragit RS, into delayed release pellets which are resistant to gastric fluid.

3 kg of these delayed release pellets (active ingredient content 59.1% by weight) and 3 kg of non-delayed pellets (active ingredient content 68% by weight) are cautiously sprayed with water in a spheronizer and then coated with a powdered mixture of 60 g of talc and 60 g of sodium carboxymethylcellulose (Blanose 7H4, 8000 mPa·s, average particle size 20 μm).

The particles then, in a stream of air and with rotation of the spheronizer disc, have a suspension of the following composition poured over them:

30 g of aspartame, 45 g of citric acid, 50 g of dry vanillin flavour, 150 g of hydroxyethylcellulose (particle size 25 μm, 4500 mPa·s), 75 g of talc, 75 g of polyvinylpyrrolidone K 25 and 650 g of ethanol.

The resulting pellets, which have an active ingredient content of about 58% by weight, are packed in a pellet dispenser which meters about 860 mg with a half turn of the metering head, and about 1720 mg with a full turn, onto, for example, a spoon (equivalent to 500 and 1000 mg of amoxicillin respectively). When the pellets are placed on the tongue using the spoon they produce spontaneous salivation and are converted into a soft, fruit-flavoured pellet paste which can easily be swallowed.

EXAMPLE 14

Sieved ascorbic acid crystals are rounded off in a fluidized bed apparatus with a concentrated aqueous solution of ascorbic acid. After drying, the ascorbic acid fraction with a particle size of from 0.315 to 0.7 mm (10 kg) in a spheronizer has a suspension of the following composition slowly poured over it, and is dried in a stream of air:

150 g of aspartame,
150 g of lemon flavour,
250 g of methylhydroxypropylcellulose (4500 mPa·s),
50 g of talc,
50 g of polyvinylpyrrolidone K 25 and
1400 g of ethanol.

The sieved and dried material is packed in a pellet dispenser whose metering chambers are adjusted so that an amount of pellets (532 mg) containing 500 mg of ascorbic acid is metered on turning through 180°. If this is placed on the tongue there is production, through spontaneous salivation, of a lemon-flavoured, coherent, sour-sweet pallet paste which can easily be swallowed.

EXAMPLE 15

10 kg of citric acid crystals with a particle size of from 0.25 to 0.6 mm are introduced into a vacuum wet mixer. After the crystals have been moistened with ethanol they are stirred until a sticky mass is produced. This is dusted with calcium carbonate powder, whereupon the calcium carbonate binds completely to the citric acid crystals. After remoistening with ethanol, dusting with calcium carbonate is repeated. This finally results in well-rounded calcium carbonate pellets with a citric acid core. In total, 5.8 kg of calcium carbonate are applied in this process.

In the same apparatus, 15 kg of sieved calcium carbonate/citric acid pellets (0.4–1.0 mm fraction) are coated while stirring in vacuo with a suspension of 200 g of citric acid,
150 g of aspartame,
150 g of lemon flavour,
50 g of orange flavour,
450 g of sodium carboxymethylcellulose (Blanose 7H4, 8000 mPa·s, average particle size 20 µm),
200 g of talc and
1900 g of ethanol and are dried at the same time.

The resulting pellets can, for example, be placed in a pellet dispenser whose metering chambers are adjusted so that 2.350 g of calcium carbonate pellets which contain the recommended daily dose of 800 mg of calcium are metered by turning through 3600. When the pellets are placed on the tongue, for example with the aid of a spoon, the salivation which rapidly starts produces a soft pellet mass which can be swallowed very easily.

It is possible in an analogous manner to obtain, by using magnesium carbonate in place of calcium carbonate, corresponding magnesium carbonate pellets and to place them, for example, in a pellet dispenser which meters, with a half turn, 1.25 g of pellets which contain 5 mmol (120 mg) of magnesium.

EXAMPLE 16

14 kg of citric acid crystals are coated in a vacuum granulator in a manner analogous to Example 15 but with 1.4 kg of vitamin mix containing the vitamins $B_1$, $B_2$, $B_6$, $B_{12}$, folic acid, vitamin E, biotin, vitamin C, pantothenic acid, niacin and, as carrier, maltodextrin, in place of calcium carbonate. 200 mg of the vitamin mix contain the daily requirement of said vitamins.

Without sieving, the coated citric acid/vitamin pellets are coated in the same apparatus with a suspension of 60 g of tartaric acid,
70 g of sodium cyclamate,
70 of orange flavour,
70 g of talc,
100 g of polyvinylpyrrolidone K 25,
400 g of methylhydroxypropylcellulose (Methocel E 6, 6 mPa·s) and
2100 g of ethanol and dried in vacuo.

The coated pellets can, for example, be placed in a pellet dispenser whose metering chambers are adjusted so that, on turning through 360°, 2.34 g of pellets which contain the recommended daily dose of said vitamins are metered. If the pellets are placed with a spoon on the tongue, they produce within 10 seconds a soft, coherent pellet paste which has a fruity flavour of oranges and can easily be swallowed.

What is claimed is:

1. A pharmaceutical composition for oral administration, which forms, when placed in contact with saliva, a coherent, mouldable, viscous, plastic mass which is slippery on the surface and does not adhere to the oral mucosa, comprising (A) a plurality of particles comprising at least one pharmaceutically active ingredient selected from the group consisting of digestion-promoting agents, antibiotics, vitamins, analgesics and antirheumatics, and (B) a coating consisting essentially of two or more coating layers and surrounding said particles thereby forming a plurality of coated particles, wherein (a) each coating layer comprises at least one hydratable, pharmaceutically acceptable polymer selected from the group consisting of sodium carboxymethylcellulose having a viscosity of from 2500 to 8000 mPa·s, measured as 1% (weight/weight) aqueous solution of 25° C., a degree of polymerisation of from 500 to 2000, and 0.45 to 1.45 carboxymethyl groups per anhydroglucose unit and xanthan having a viscosity of from 25 to 3000 mPa·s, measured as 1% (weight/weight) aqueous solution at 25° C. and a pH of about 6, and a molecular weight of more than 1,000,000, which envelops the active ingredient-containing particle or the active ingredient-containing particles, and which prevents active ingredient-containing particles from escaping from the mass and active ingredient from being released in the mouth, and (b) the outermost of the coating layers comprises an effective amount of at least one salivation-promoting agent, wherein the hydratable polymer and the salivation-promoting agent and their amounts are selected such that, on contact with saliva, said coherent, mouldable, viscous, plastic mass is formed within less than 20 seconds.

2. The pharmaceutical composition according to claim 1, wherein the pharmaceutically active ingredient is selected from the group consisting of 5-aminosalicylic acid, amoxicillin, cefaclor, ascorbic acid, acetylsalicyltc acid, and ibuprofen.

3. A pharmaceutical composition for oral administration which forms, when placed in contact with saliva, a coherent, mouldable, viscous, plastic mass which is slippery on the surface and does not adhere to the oral mucosa, comprising
- (A) a plurality of particles comprising 5-aminosalicylic acid as a pharmaceutically active ingredient, and
- (B) a coating consisting essentially of two or more coating layers and surrounding said particles thereby forming a plurality of coated particles, wherein
  - (a) each coating layer comprises at least one hydratable, pharmaceutically acceptable sodium carboxymethylcellulose polymer having a viscosity of from 2500 to 8000 mPa·s, measured as 1% (weight/weight) aqueous solution of 25° C. a degree of polymerisation of from 500 to 2000, and 0.45 to 1.45 carboxymethyl groups per anhydroglucose unit, which envelops the active ingredient-containing particle or the active ingredient-containing particles, and which prevents active ingredient-containing particles from escaping from the mass and active ingredient from being released in the mouth, and
  - (b) the outermost of the coating layers comprises an effective amount of at least one salivation-promoting agent, wherein
    the hydratable polymer and the salivation-promoting agent and their amounts are selected such that, on contact with saliva, said coherent, mouldable, viscous, plastic mass is formed within less than 20 seconds.

4. The pharmaceutical composition according to claim 3, wherein the salivation-promoting agent is a water-soluble organic acid.

5. A pharmaceutical composition for oral administration, which forms, when placed in contact with saliva, a coherent, mouldable, viscous, plastic mass which is slippery on the surface and does not adhere to the oral mucosa, comprising
- (A) a plurality of particles comprising at least one pharmaceutically active ingredient selected from the group consisting of amoxicillin and cefaclor, and
- (B) a coating consisting essentially of two or more coating layers and surrounding said particles thereby forming a plurality of coated particles, wherein
  - (a) each coating layer comprises at least one hydratable, pharmceutically acceptable xanthan polymer having a viscosity of from 25 to 3000 mPa·s, measured as 1% (weight/weight) aqueous solution at 25° C. and a pH of about 6, and a molecular weight of more than 1,000,000 which envelops the active ingredient-containing particle or the active ingredient-containing particles, and which prevents active ingredient-containing particles from escaping from the mass and active ingredient from being released in the mouth, and
  - (b) the outermost of the coating layers comprises an effective amount of at least one salivation-promoting agent, wherein
    the hydratable polymer and the salivation-promoting agent and their amounts are selected such that, on contact with saliva, said coherent, mouldable, viscous, plastic mass is formed within less than 20 seconds.

6. A pharmaceutical composition for oral administration, which forms, when placed in contact with saliva, a coherent, mouldable, viscous, plastic mass which is slippery on the surface and does not adhere to the oral mucasa, comprising
- (A) a core comprising a digestion-promoting agent and
- (B) a coating consisting essentially of two or more coating layers and surrounding said core thereby forming a coated particle, wherein
  - (a) each coating layer comprises at least one hydratable, pharmaceutically acceptable sodium carboxymethylcellulose polymer having a viscosity of from 2500 to 8000 mPa·s, measured as 1% (weight/weight) aqueous solution of 25° C., a degree of polymerisation of from 500 to 2000, and 0.45 to 1.45 carboxymethyl groups per anhydroglucose unit, which envelops the active ingredient-containing particle or the active ingredient-containing particles, and which prevents active ingredient-containing particles from escaping from the mass and active ingredient from being released in the mouth, and
  - (b) the outermost of the coating layers comprises an effective amount of at least one salivation-promoting agent, wherein
    the hydratable polymer and the salivation-promoting agent and their amounts are selected such that, on contact with saliva, said coherent, mouldable, viscous, plastic mass is formed within less than 20 seconds.

7. The pharmaceutical composition according to claim 6, wherein the digestion-promoting agent is loperamide.

8. The pharmaceutical composition according to claim 6, wherein the salivation-promoting agent is a water-soluble organic acid.

9. A pharmaceutical composition for oral administration, which forms, when placed in contact with saliva, a coherent, mouldable, viscous, plastic mass which is slippery on the surface and does not adhere to the oral mucosa, comprising
- (A) a core comprising at least one pharmaceutically active ingredient selected from the group consisting of vitamins, analgesics and antirheumatics, and
- (B) a coating consisting essentially of two or more coating layers and surrounding said core thereby forming a coated particle, wherein
  - (a) each coating layer comprises at least one hydratable, pharmaceutically acceptable polymer selected from the group consisting of polyacrylic acids having a viscosity of from 5000 to 30,000 mPa·s, measured as 1% (weight/weight) aqueous solution at 25° C., and molecular weight of from 400,000 to 4,000,000, which envelopes the active ingredient-containing particle or the active ingredient-containing particles, and which prevents active ingredient-containing particles from escaping from the mass and active ingredient from being released in the mouth, and
  - (b) the outermost of the coating layers comprises an effective amount of at least one salivation-promoting agent, wherein
    the hydratable polymer and the salivation-promoting agent and their amounts are selected such that, on contact with saliva, said coherent, mouldable, viscous, plastic mass is formed within less than 20 seconds.

10. The pharmaceutical composition according to claim 9, wherein the pharmaceutically active ingredient is acetylsalicylic acid.

11. The pharmaceutical composition according to claim 9, wherein the core comprises ascorbic acid, folic acid, vitamin E, and vitamin $B_1$, $B_2$, $B_6$ and $B_{12}$.

12. A pharmaceutical composition for oral administration, which forms, when placed in contact with saliva, a coherent, mouldable, viscous, plastic mass which is slippery on the surface and does not adhere to the oral mucosa, comprising (A) a core comprising at least one pharmaceutically active ingredient selected from the group consisting of vitamins, analgesics and antirheumatics, and (B) a coating consisting essentially of two or more coating layers and surrounding said core thereby forming a coated particle, wherein (a) each coating layer comprises at least one hydratable, pharmaceutically acceptable polymer selected from the group consisting of polyacrylates having a molecular weight of from 400,000 to 4,000,000, a viscosity measured as 1% (weight/weight) aqueous solution, of from 25 to 30,000 mPa·s, which envelopes the active ingredient-containing particle or the active ingredient-containing particles, and which prevents active ingredient-containing particles from escaping from the mass and active ingredient from being released in the mouth, and (b) the outermost of the coating layers comprises an effective amount of at least one salivation-promoting agent, wherein the hydratable polymer and the salivation-promoting agent and their amounts are selected such that, on contact with saliva, said coherent, mouldable, viscous, plastic mass is formed within less than 20 seconds.

* * * * *